US00PP13258P3

(12) United States Plant Patent
Vandenberg

(10) Patent No.: US PP13,258 P3
(45) Date of Patent: Nov. 19, 2002

(54) ROSE PLANT NAMED 'YOREDA'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/821,998

(22) Filed: Mar. 31, 2001

(65) Prior Publication Data

US 2002/0144319 P1 Oct. 3, 2002

(51) Int. Cl.[7] ..... A01H 5/00

(52) U.S. Cl. ..... Plt./140

(58) Field of Search ..... Plt./140, 139, 130

*Primary Examiner*—Bruce R. Campell
*Assistant Examiner*—June Hwu
(74) *Attorney, Agent, or Firm*—C. A. Whealy

(57) ABSTRACT

A distinctive cultivar of Hybrid Tea Rose plant named 'Yoreda', characterized by its glossy dark green leaves; long and dark red stems; velvety dark red-colored flowers; and good postproduction longevity.

1 Drawing Sheet

BOTANICAL CLASSIFICATION/CULTIVAR DESIGNATION

*Rosa hybrida* cultivar Yoreda.

BACKGROUND OF THE INVENTION

The present invention relates to a new and distinct cultivar of Hybrid Tea Rose plant, botanically known as *Rosa hybrida,* commercially produced as a cut flower, and hereinafter referred to by the name 'Yoreda'.

The new cultivar is a product of a planned breeding program conducted by the Inventor in Salinas, Calif. The objective of the breeding program was to develop new cut Rose cultivars with attractive flower petal colors, long and strong stems, dark green leaves and good postproduction longevity.

The new cultivar originated from a cross made by the Inventor in 1997 of the Rose cultivar Korpek, not patented, as the female, or seed, parent with an unnamed proprietary selection as the male, or pollen, parent. The cultivar Yoreda was discovered and selected by the Inventor as a flowering plant within the progeny of the stated cross in a controlled environment in April, 1999, in Madrid, Cundinamarca, Colombia.

Since March, 2000, asexual reproduction of the new cultivar by grafting on *Rosa Manetti* rootstocks in Madrid, Cundinamarca, Colombia, has shown that the unique features of the new cultivar are stable and reproduced true to type in successive generations of asexual reproduction.

SUMMARY OF THE INVENTION

The following traits have been repeatedly observed and are determined to be the unique characteristics of 'Yoreda'. These characteristics in combination distinguish the new Hybrid Tea Rose as a new and distinct cultivar:

1. Glossy dark green leaves.
2. Long and dark red stems.
3. Velvety dark red flowers.
4. Good postproduction longevity.

Plants of the Hybrid Tea Rose can be compared to plants of the female parent, the cultivar Korpek. In side-by-side comparisons conducted by the Inventor in Salinas, Calif., plants of the new cultivar differed from plants of the cultivar Korpek in the following characteristics:

1. Plants of the new Hybrid Tea Rose have longer flowering stems than plants of the cultivar Korpek.
2. Plants of the new Hybrid Tea Rose have larger flowers than plants of the cultivar Korpek.
3. Plants of the new Hybrid Tea Rose have darker red-colored flower petals than plants of the cultivar Korpek.

Plants of the Hybrid Tea Rose can be compared to plants of the male parent, an unnamed proprietary selection. In side-by-side comparisons conducted by the Inventor in Salinas, Calif., plants of the new cultivar differed from plants of the unnamed proprietary selection in the following characteristics:

1. Plants of the new Hybrid Tea Rose have longer flowering stems than plants of the unnamed proprietary selection.
2. Plants of the new Hybrid Tea Rose have larger flowers than plants of the unnamed proprietary selection.
3. Plants of the new Hybrid Tea Rose have darker red-colored flower petals than plants of the unnamed proprietary selection.

Plants of the new Hybrid Tea Rose have not been observed under all possible environmental conditions. The phenotype may vary significantly with variations in environment such as temperature, light, water status and/or fertilizer type and rate, without, however, any variance in genotype.

BRIEF DESCRIPTION OF PHOTOGRAPH

The accompanying colored photograph illustrates the new Hybrid Tea Rose plant, showing the colors as true as it is reasonably possible to obtain in colored reproductions of this type. Colors in the photograph may differ slightly from the color values cited in the detailed botanical description which accurately describe the colors of the new Hybrid Tea Rose.

The photograph comprises a side perspective view of a typical flowering stem of the new Hybrid Tea Rose grown in Madrid, Cundinamarca, Colombia.

DETAILED BOTANICAL DESCRIPTION

The following observations and measurements describe cut flowering stems of plants grown in Madrid, Cundinamarca, Colombia, in polyethylene-covered greenhouses with day temperatures ranging from 14 to 20° C., night temperatures ranging from 4 to 8° C., and light levels ranging from 3,000 to 5,000 foot-candles. Flowering stems used in the photograph and the description were about 75 days old. In the following description, color references are made to The Royal Horticultural Society Colour Chart except where general terms of ordinary dictionary significance are used.

Classification:

*Botanical.*—*Rosa hybrida* cultivar Yoreda.

*Commercial.*—Hybrid Tea Rose used as a cut flower.

Parentage:

*Female, or seed, parent.*—*Rosa hybrida* cultivar Korpek, not patented.

*Male, or pollen, parent.*—Unnamed *Rosa hybrida* proprietary selection, not patented.

Propagation:

*Type.*—Cuttings grafted onto *Rosa Manetti* rootstocks.

Plant description:

*Form.*—Upright; narrow.

*Growth habit.*—Moderately vigorous.

*Plant height.*—About 99 to 107 cm.

*Plant width.*—About 20 cm.

*Stem and lateral branches (peduncles).*—Lateral branch length: About 99 to 107 cm. Lateral branch diameter: Base: About 7.5 mm. Apex: About 5 mm. Internode length: About 4.6 cm. Texture: Smooth. Strength: Strong. Color: Young: 146A overlain with 187A. Mature: Close to 187A. Thorns. Quantity: About 3 per 12 cm of stem. Height: About 5 mm. Width at base: About 6 mm. Shape: Deltoid. Color, immature and mature: 59A.

*Foliage description.*—Arrangement: Alternate, compound with typically three to five leaflets per leaf. Leaf length, five-leaflet leaves: Terminal leaves: About 9.5 cm. Lateral leaves: About 7.7 cm. Leaf width, five-leaflet leaves: Terminal leaves: About 5.7 cm. Lateral leaves: About 4.5 cm. Leaflet shape: Ovate. Leaflet apex: Acuminate. Leaflet base: Obtuse. Leaflet margin: Sharply serrate. Leaflet texture: Smooth, leathery, glabrous. Occasional small thorns on lower petiole and midrib of terminal leaflet, about 2 by 2 mm in size and 59A in color. Petiole length, 5-leaflet leaves: About 8.9 cm. Petiole diameter: At stem attachment: About 6.5 mm. At base of terminal leaves: About 1.5 mm. Stipules: Quantity: Two at base of petiole. Length: About 2 cm. Length of appendages: About 7.5 mm. Width: About 2 mm. Color: Young and mature foliage, upper surface: Darker than 147A, glossy; venation, 147A to 147B. Young and mature foliage, lower surface: Close to 147B; venation, 146C. Petiole: Upper surface: Close to 187A. Lower surface: 146A to 146B; nodes, close to 187A. Stipule, upper surface: Darker than 147A. Stipule, lower surface: Close to 147B.

Flower description:

*Flower type and habit.*—Dark red velvety flowers. Consistently symmetrical rosette flowers. Freely and recurrent flowering. Flowers arranged singly at terminal apices. Flowers persistent.

*Flowering season/time to flower.*—Year-round under greenhouse conditions. Depending on environmental conditions and season, time to flower is about 75 days.

*Flower diameter, fully opened.*—About 11 cm.

*Flower depth (height), fully opened.*—About 5.3 cm.

*Flower longevity as a cut flower.*—At least 8 to 10 days.

*Fragrance.*—Moderate, typical Hybrid Tea Rose fragrance.

*Flower buds.*—Shape: Ovoid. Length: About 5.7 cm. Color: 144A.

*Petals and petaloids.*—Petaloids vary in size, but similar to petals in shape and coloration. Quantity: About 29. Length, outer petals: About 5.3 cm. Width, outer petals: About 5.9 cm. Shape: Roughly obovate to almost circular. Apex: Rounded or slightly emarginate. Margin: Mostly entire, slightly reflexed. Texture: Smooth, velvety. Color: When opening, upper and lower surfaces: More intense than 46A to 53A; iridescent. Fully opened, upper and lower surfaces: Dulled 46A to 53A; towards base, close to 155A; petal color does not fade with sebsequent development.

*Sepals.*—Quantity: Five. Length: About 4.7 cm. Diameter: About 1.3 cm. Shape: Sharply lanceolate. Apex: Elongated, acuminate. Base: Fused at receptacle. Margin: Ciliate with occasional sharply acuminate appendages. Texture: Upper surface, pubescent; lower surface, slightly pubescent. Color: Upper surface: Closest to 144B. Lower surface: 144A with central longitudinal stripe, 59A.

*Reproductive organs.*—Stamens: Quantity: About 122 per flower. Anther length: About 3 mm. Anther diameter: About 2 mm. Anther shape: Cordate, concave. Anther color: Close to 14A. Filament length: About 3 mm. Filament color: Close to 53A. Pollen amount: None. Pistils: Quantity: About 105 per flower. Pistil length: About 1.1 cm. Style color: Close to 45A. Stigma shape: Bi-lobed. Stigma color: Close to 5D. Ovary color: 145D to 155D. Receptacle height: About 1.1 cm. Receptacle diameter: About 1.2 cm. Receptacle texture: Smooth. Receptacle color: 144A.

*Seed.*—None observed.

Disease resistance: Plants of the new Hybrid Tea Rose have been observed to be somewhat resistant to Powdery Mildew.

It is claimed:

1. A new and distinct Hybrid Tea Rose plant named 'Yoreda', as illustrated and described.

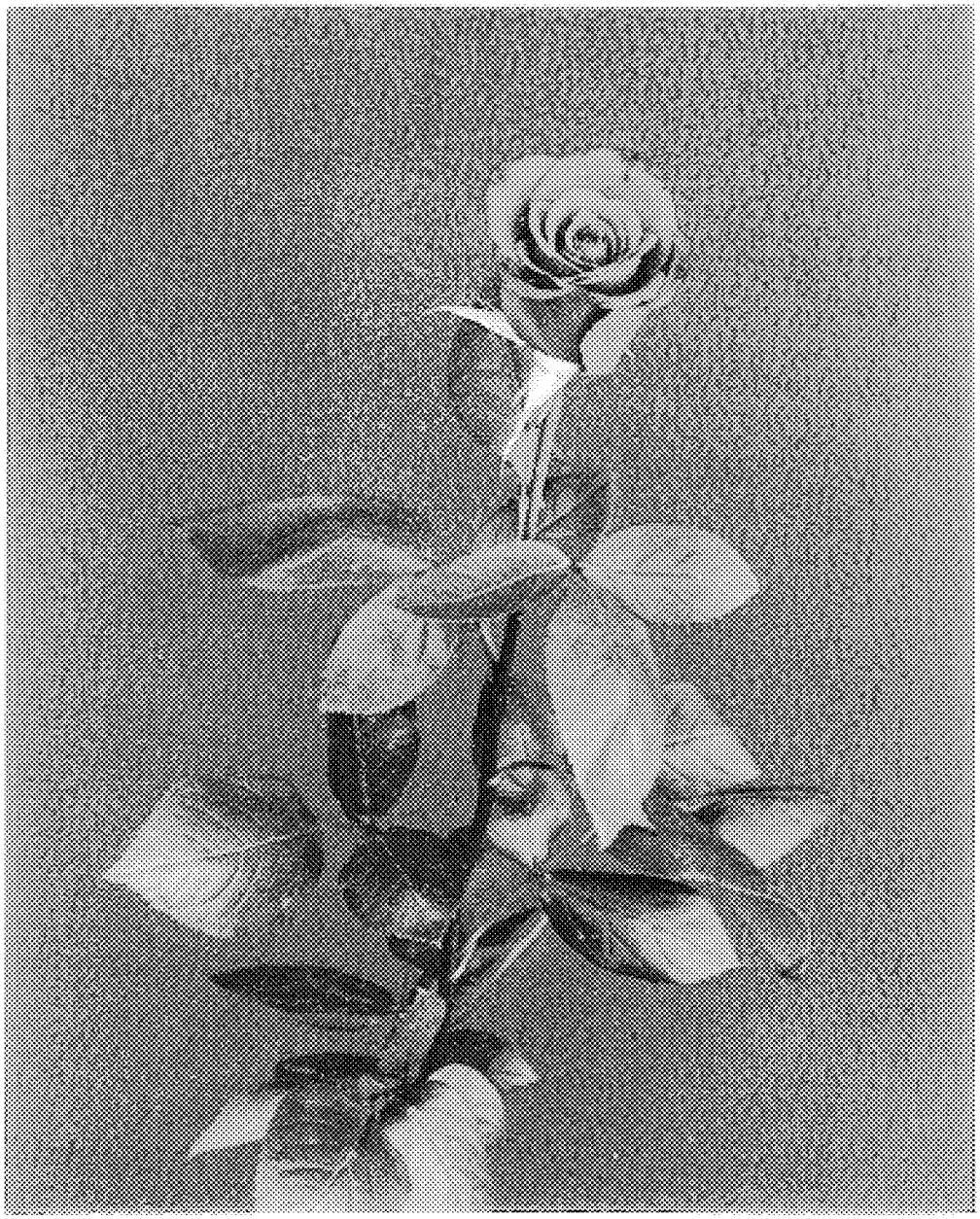

* * * * *